(12) United States Patent
Fontana et al.

(10) Patent No.: US 8,674,006 B2
(45) Date of Patent: Mar. 18, 2014

(54) BLACK PIGMENT DISPERSION

(75) Inventors: Margherita Fontana, Thalwil (CH); Marian Lanz, Röschenz (CH); Frank Oliver Heinrich Pirrung, Grünstadt (DE); Andreas Gernandt, Ludwigshafen (DE); Dario Perera, Basel (CH); Thomas Ruch, Delémont (CH); Christoph Krebs, Pratteln (CH); Thomas Eichenberger, Basel (CH); Bernd Lamatsch, Riehen (CH); Achim Lamatsch, legal representative, Waldkirch (DE)

(73) Assignee: BASF SE Ludwigshafen (DE)

( * ) Notice: Subject to any disclaimer, the term of this patent is extended or adjusted under 35 U.S.C. 154(b) by 237 days.

(21) Appl. No.: 13/144,106

(22) PCT Filed: Jan. 7, 2010

(86) PCT No.: PCT/EP2010/050089
§ 371 (c)(1), (2), (4) Date: Nov. 16, 2011

(87) PCT Pub. No.: WO2010/081756
PCT Pub. Date: Jul. 22, 2010

(65) Prior Publication Data
US 2012/0172498 A1    Jul. 5, 2012

(30) Foreign Application Priority Data
Jan. 19, 2009   (EP) .................................. 09150843

(51) Int. Cl.
*C08K 5/34*     (2006.01)
*C07D 405/00*   (2006.01)

(52) U.S. Cl.
USPC ........................................... 524/94; 548/456

(58) Field of Classification Search
USPC ....................................................... 524/94
See application file for complete search history.

(56) References Cited

U.S. PATENT DOCUMENTS

| 4,115,404 | A | 9/1978 | Greenhalgh et al. |
| 6,503,937 | B1 | 1/2003 | Nesvadba |
| 6,524,382 | B1 | 2/2003 | Bujard et al. |
| 7,952,791 | B2 * | 5/2011 | Yanagisawa et al. ......... 359/296 |
| 2003/0105201 | A1 | 6/2003 | Auschra |
| 2009/0221739 | A1* | 9/2009 | Knischka et al. ............. 524/505 |
| 2009/0296195 | A1 | 12/2009 | Fontana |
| 2010/0186891 | A1* | 7/2010 | Ruch et al. ................. 156/272.8 |
| 2010/0265564 | A1 | 10/2010 | Fontana et al. |
| 2010/0290103 | A1 | 11/2010 | Fontana et al. |

FOREIGN PATENT DOCUMENTS

| DE | 27 10 464 A1 | 9/1977 |
| JP | 08 048893 A | 2/1996 |
| JP | 09193547 A | 7/1997 |
| JP | 2007 266411 A | 10/2007 |
| WO | 00/24736 A1 | 5/2000 |
| WO | 01/32577 A1 | 5/2001 |
| WO | 2006/074969 A1 | 7/2006 |
| WO | 2008/003604 A2 | 1/2008 |
| WO | 2010/081625 A2 | 7/2010 |

OTHER PUBLICATIONS

English Lang. Abstr of JP 2007 266411 Oct. 11, 2007.
English Lang. Abstr of JP 09193547 Jul. 29, 1997.
English Lang. Abstr of JP 08 048893 Feb. 20, 1996.
Hawker et al., Chemical Reviews vol. 101, (Jan. 1, 2001), pp. 3661-3688.

\* cited by examiner

*Primary Examiner* — Hui Chin
(74) *Attorney, Agent, or Firm* — Shruti Costales

(57) ABSTRACT

Described is a pigment dispersion which is useful for electrophoretic displays comprising α) a bis-oxodihydro-indolylene-benzodifuranone colorant of the Formula (I) wherein the substituents are defined as in claim 1, β) a specific polymeric dispersant, and γ) a solvent which is suitable for dispersions used in electrophoretic displays. Also described are novel colourants and dispersants.

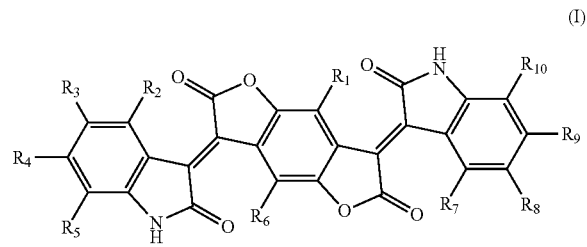

10 Claims, 1 Drawing Sheet

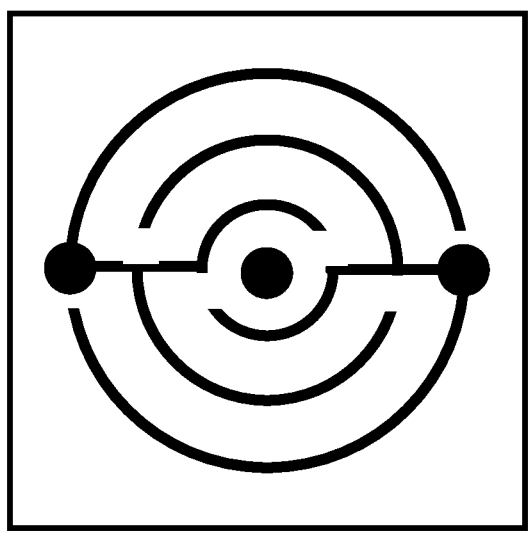

BLACK PIGMENT DISPERSION

The invention relates to a pigment dispersion, especially a black pigment dispersion, comprising a bis-oxodihydro-indolylene-benzodifuranone colourant, a specific dispersant, and a suitable solvent, the use of said dispersion, colourants and/or dispersants in electro-phoretic displays, and to novel bis-oxodihydro-indolylene-benzodifuranone colourants and dispersants.

As discussed in U.S. Pat. No. 7,002,728 B2, the presently preferred form of electrophoretic medium comprises white titania and carbon black particles in a hydrocarbon suspending fluid, this hydrocarbon being used alone or in admixture with a chlorinated hydrocarbon or other low dielectric constant fluid. Most other prior art electrophoretic displays which require a black pigment have also used carbon black for this purpose, apparently largely because the material is readily available in mass quantities and very inexpensive. However, a number of problems with prior art electrophoretic displays are associated with the use of carbon black for the black electrophoretic particles. Carbon black has a complex and poorly understood surface chemistry, which may vary widely with the specific raw material (typically petroleum) and the exact process used for the carbon black production. Carbon black pigment particles also have a poorly understood aggregate, fractal structure. Furthermore, carbon black is notoriously effective in adsorbing gases and liquids with which it comes into contact, and such adsorbed gases and liquids can change the physicochemical properties of the carbon black surface. Hence, it is difficult to ensure consistent surface properties of carbon black from batch to batch. This is especially problematic in electrophoretic displays, since the electrophoretic particles used are typically so small (of the order of 1 μm) that their properties are dominated by the properties of their surfaces.

As also stated in U.S. Pat. No. 7,002,758 carbon black presents certain peculiar difficulties in obtaining proper charging of particles in opposite charge dual particle electrophoretic displays. Specifically, it has been found that when using carbon black and titania as the black and white particles respectively in an opposite charge dual particle electrophoretic display, combinations of charging agents and other materials which produce all positively charged carbon black particles tend to produce a minor proportion of titania particles which are also positively charged. The resultant mixture of negatively and positively charged titania particles leads to contamination of the extreme optical states of the medium, thus adversely affecting its contrast ratio.

Carbon black is also known to have electrical conductivity, not only in bulk, but also dispersed in polymers, at least to an extent to give antistatic properties (S. P. Rwei et al., *Colloid. Polym. Sci.* 2002, 280, pages 1110-1115) and also in a dispersion in mineral oils (*J. Electroanal. Chem.* 2005, 577, 67-78). This means that an electric current will flow through the dispersion upon application of an electric field, leading either to a break-down of the field and, hence, the orientation of the particles (in case of a field once applied without continuously keeping a certain voltage) or requiring electrical energy to compensate for this.

There is thus a need for a black particle for use in electrophoretic media that does not suffer from the problems associated with the use of carbon black, e.g. for a dispersion of a black particle, said dispersion having low electrical conductivity, i.e. a high resistance. However, the search for such a black particle is subject to considerable difficulties. Although the optical properties of numerous pigments are of course known from their use in the paint and similar industries, a pigment for use in an electrophoretic display must possess several properties in addition to appropriate optical properties. The pigment must be compatible with the numerous other components of the electrophoretic medium, including the suspending fluid, any other pigment particles present, charge control agents and surfactants typically present in the suspending fluid, and the capsule wall material (if a capsule wall is present). The pigment particles must also be able to sustain a charge when suspended in the suspending fluid, and the zeta potentials of the particles caused by such charges should all be of the same polarity and should not extend over an excessively wide range, or the electrophoretic medium may not have desirable electro-optic properties; for example, if some particles have very low zeta potentials, a very long driving pulse may be required to move such particles to a desired position within the electrophoretic medium, resulting in slow switching of the medium. It will be appreciated that such information relating to the ability of pigment particles to acquire and hold charges is not available for most pigments potentially usable in an electrophoretic display, since such electrical properties are irrelevant to the normal commercial uses of the pigments.

The same arguments are also valid, if the partner of the black pigment is not a white, but a colored particle, and for this display Yellow/Black, Red/Black, Green/Black and Blue/Black particles systems are needed with the same characteristics as the above-mentioned Black/White systems.

It has now surprisingly been found that a composition comprising certain specific dispersants and certain bis-oxodihydro-indolylene-benzodifuranone colourants, said colourants being generically described in WO 00/24736 A1, or the "violet powder" specifically described in Example 12b thereof can be used as replacement for carbon black in electrophoretic displays. Thus, in the presence of suitable additives (dispersants) dispersions of a purely organic black pigment in media with low conductivity and low permittivity can be prepared, which show electrophoretic mobility under the influence of an electric field and, hence, can be used as black pigment for electrophoretic display applications, with lower conductivity and thus lower power consumption than the state of the art.

DESCRIPTION OF THE DRAWING

FIG. 1 illustrates the three-point electrode geometry in one particular well of a 96-well-plate (cf. Example 11 for more information). The big spots represent the connection points for the electrodes. The resistance is measured between the half-circle electrodes, the center electrode serving for grounding.

The invention relates to a dispersion which is useful for electrophoretic displays, especially a dispersion wherein the dispersed particles have a diameter of 100 to 1000 nm (nanometers) preferably 200-800 nm, most preferably 300-600 nm, comprising α) a bis-oxodihydro-indolylene-benzodifuranone colourant of the formula I

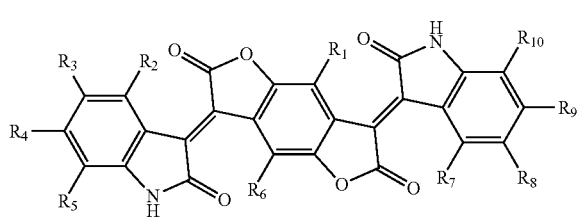 (I)

wherein $R_1$ and $R_6$ are each independently of the other H, $CH_3$, $CF_3$, F or Cl, preferably H or F, most preferably H; $R_2$, $R_3$, $R_4$, $R_5$, $R_7$, $R_8$, $R_9$ and $R_{10}$ are each independently of all others H, halogen, $R_{11}$, COOH, $COOR_{11}$, $COO^-$, $CONH_2$, $CONHR_{11}$, $CONR_{11}R_{12}$, CN, OH, $OR_{11}$, $OOCR_{11}$, $OOCNH_2$, $OOCNHR_{11}$, $OOCNR_{11}R_{12}$, $NO_2$, $NH_2$, $NHR_{11}$, $NR_{11}R_{12}$, $NHCOR_{12}$, $NR_{11}COR_{12}$, $N=CH_2$, $N=CHR_{11}$, $N=CR_{11}R_{12}$, SH, $SR_{11}$, $SOR_{11}$, $SO_2R_{11}$, $SO_3R_{11}$, $SO_3H$, $SO_3^-$, $SO_2NH_2$, $SO_2NHR_{11}$ or $SO_2NR_{11}R_{12}$; and $R_2$ and $R_3$, $R_3$ and $R_4$, $R_4$ and $R_5$, $R_7$ and $R_8$, $R_8$ and $R_9$, and/or $R_9$ and $R_{10}$ can also be linked together by a direct bond or an O, S, NH or $NR_{11}$ bridge; $R_{11}$ and $R_{12}$ are each independently of the other $C_1$-$C_{12}$alkyl, $C_1$-$C_{12}$cycloalkyl, $C_1$-$C_{12}$alkenyl, $C_1$-$C_{12}$cycloalkenyl or $C_1$-$C_{12}$alkinyl, each of which is uninterrupted or interrupted by oxygen, NH, $NR_{13}$ and/or sulfur in two or more fragments each comprising at least 2 C atoms, and each of which is also unsubstituted or substituted one or more times with COOH, $COOR_{13}$, $COO^-$, $CONH_2$, $CONHR_{13}$, $CONR_{13}R_{14}$, CN, oxo, OH, $OR_{13}$, $OOCR_{13}$, $OOCNH_2$, $OOCNHR_{13}$, $OOCNR_{13}R_{14}$, $NR_{13}$, $NH_2$, $NHR_{13}$, $NR_{13}R_{14}$, $NHCOR_{14}$, $NR_{13}COR_{14}$, $N=CH_2$, $N=CHR_{13}$, $N=CR_{13}R_{14}$, SH, $SR_{13}$, $SOR_{13}$, $SO_2R_{13}$, $SO_3R_{13}$, $SO_3H$, $SO_3^-$, $SO_2NH_2$, $SO_2NHR_{13}$, $SO_2NR_{13}R_{14}$ or halogen; or $C_7$-$C_{12}$aralkyl, $C_1$-$C_{11}$heteroaryl or $C_6$-$C_{12}$aryl, each of which is unsubstituted or substituted one or more times with COOH, $COOR_{13}$, $COO^-$, $CONH_2$, $CONHR_{13}$, $CONR_{13}R_{14}$, CN, OH, $OR_{13}$, $OOCR_{13}$, $OOCNH_2$, $OOCNHR_{13}$, $OOCNR_{13}R_{14}$, $NO_2$, $NH_2$, $NHR_{13}$, $NR_{13}R_{14}$, $NHCOR_{14}$, $NR_{13}COR_{14}$, $N=CH_2$, $N=CHR_{13}$, $N=CR_{13}R_{14}$, SH, $SR_{13}$, $SOR_{13}$, $SO_2R_{13}$, $SO_3R_{13}$, $SO_3H$, $SO_3^-$, $SO_2NH_2$, $SO_2NHR_{13}$, $SO_2NR_{13}R_{14}$ or halogen; and each $R_{13}$ or $R_{14}$ is, independently of any other $R_{13}$ or $R_{14}$, $C_1$-$C_6$alkyl, benzyl or phenyl, each of which is unsubstituted or substituted one or more times with substituents as defined above, with the proviso that the total number of atoms in any substituent of $R_{13}$ and $R_{14}$ is from 1 to 8; whereby pairs of substituents selected from the group consisting of all $R_{13}$ and $R_{14}$ can optionally be linked together by a direct bond or an O, S, NH or $NR_{11}$ bridge so as to form rings, or a cis-trans isomer thereof or a salt of such colourant or isomer having a salt-forming group, β) a polymeric dispersant comprising modified poly(meth) acrylate polymers obtainable by the process comprising the steps a1) polymerizing in a first step one or more ethylenically unsaturated monomers in the presence of at least one nitroxylether having the structural element of the formula

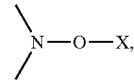

wherein X represents a group having at least one carbon atom and is such that the free radical X. derived from X is capable of initiating polymerization; or a2) polymerizing in a first step one or more ethylenically unsaturated monomers in the presence of at least one stable free nitroxyl radical of the formula

and a free radical initiator; wherein at least one monomer used in the steps a1) or a2) is a $C_1$-$C_6$ alkyl or hydroxy $C_1$-$C_6$ alkyl ester of acrylic or methacrylic acid;

and a second step b) comprising the modification of the polymer or copolymer prepared under a1) or a2) by a transesterification reaction, an amidation, hydrolysis or anhydride modification or a combination thereof, and γ) a solvent which is suitable for dispersions used in electrophoretic displays.

In the following the components of the dispersion are described in more detail.

Bis-Oxodihydro-Indolylene-Benzodifuranone Colourants.

Said cis-trans isomers of the colourant of formula I have the following core structures (omitting the substituents), the trans-trans isomer of the above formula I probably being the most stable, the cis-cis isomer probably being the least stable of said isomers.

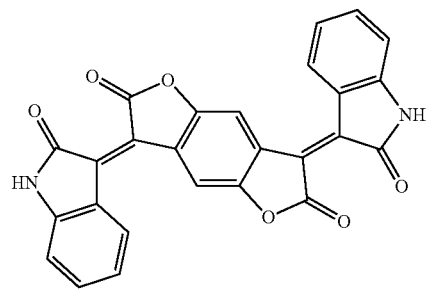

Cis-Cis

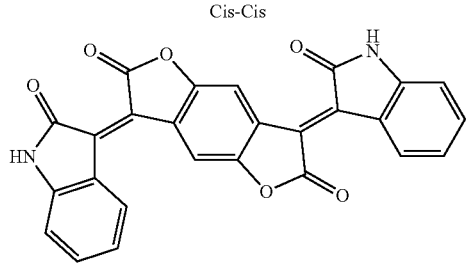

Cis-Trans

-continued

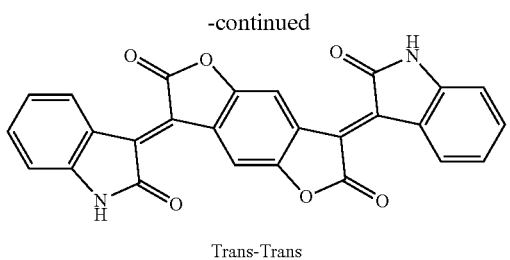

Trans-Trans

When the compound of formula (I) is anionic, its charge may be compensated by any known suitable cation, for example a metallic, organic, inorganic or metal organic cation, such as preferably an alkali, earth alkali or transition metal, ammonium, primary ammonium, secondary ammonium, ternary ammonium, e.g. trialkylammonium, quaternary ammonium, e.g. tetraalkylammonium, or an organic metal complex.

The colourants of formula (I) are both reflective and transparent to near infra-red radiation, thus limiting heat buildup, however the ratio of reflectance and transmittance depends on their particle size. The reflectance (including diffracted reflectance) is much more significant with large particles, such as those having a thickness of ≥0.4 µm, while transmittance is preponderant in the case of tiny particles, such as those having a size of from 0.01 to 0.3 µm, as well as in the case of dyes which dissolve into the substrate.

The instant colourants of formula (I) are normally obtained from the synthesis in the form of very large agglomerates and aggregates of unattractive dark colours and are highly difficult to disperse, such as the violet powder obtained according to example 12b of WO00/24736. However, it has been found that these crude powders can easily be transformed into suitable colourants just by wet-milling them with milling aids in the presence of a solvent, preferably an alcohol, amide, ester, ether or ketone, thus obtaining particles of mean size≤0.5 µm, preferably from 0.01 to 0.3 µm, which show surprisingly very attractive black hues similar to carbon black. Wet-milling can for example be performed in an attritor, such as a Dyno® or Netzsch® mill, Skandex® paint shaker or the like, for example using glass or ceramics (e.g. zirconia) pearls of size preferably from 0.1 to 3.0 mm, in particular from 0.5 to 1.0 mm. The amount of alcohol, amide, ester, ether or ketone is adequately from 0.1 to 1000 parts per part of colourant, preferably from 1 to 10 parts per part of colourant. Adequate solvents for wet-milling and/or recrystallisation are well-known in the art. The solvents disclosed for example in EP0774494, EP0934364 and WO02/068541 are specifically incorporated herein by reference.

The substituents in formula I and the general terms used in defining them have the following preferred meanings:

$R_2$, $R_4$, $R_5$, $R_7$, $R_9$, and $R_{10}$ are preferably H, F or Cl, especially H. $R_3$ and $R_8$ are preferably H, $NO_2$, $OCH_3$, $OC_2H_5$, Br, Cl, $CH_3$, $C_2H_5$, $N(CH_3)_2$, $N(CH_3)(C_2H_5)$, $N(C_2H_5)_2$, α-naphthyl, β-naphthyl or $SO_3^-$. Preferably, $R_1$ is identical to $R_6$, $R_2$ is identical to $R_7$, $R_3$ is identical to $R_8$, $R_4$ is identical to $R_9$, and/or $R_5$ is identical to $R_{10}$.

$C_1$-$C_{12}$Alkyl is, for example, methyl, ethyl, n-propyl, isopropyl, n-butyl, sec-butyl, isobutyl, tert-butyl, 2-methyl-butyl, n-pentyl, 2-pentyl, 3-pentyl, 2,2-dimethylpropyl, n-hexyl, heptyl, n-octyl, 1,1,3,3-tetramethylbutyl, 2-ethylhexyl, nonyl, decyl, undecyl or dodecyl.

$C_3$-$C_{12}$Cycloalkyl is, for example, cyclopropyl, cyclopropylmethyl, cyclobutyl, cyclopentyl, cyclohexyl, cyclohexylmethyl, trimethylcyclohexyl, thujyl, norbornyl, bornyl, norcaryl, caryl, menthyl, norpinyl, pinyl, 1-adamantyl or 2-adamantyl.

$C_2$-$C_{12}$Alkenyl is, for example, vinyl, allyl, 2-propen-2-yl, 2-buten-1-yl, 3-buten-1-yl, 1,3-butadien-2-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, or any desired isomer of hexenyl, octenyl, nonenyl, decenyl or dodecenyl.

$C_3$-$C_{12}$Cycloalkenyl is, for example, 2-cyclobuten-1-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl, 7,7-dimethyl-2,4-norcaradien-3-yl or camphenyl.

$C_2$-$C_{12}$Alkinyl is, for example, 1-propin-3-yl, 1-butin-4-yl, 1-pentin-5-yl, 2-methyl-3-butin-2-yl, 1,4-pentadiin-3-yl, 1,3-pentadiin-5-yl, 1-hexin-6-yl, cis-3-methyl-2-penten-4-in-1-yl, trans-3-methyl-2-penten-4-in-1-yl, 1,3-hexadiin-5-yl, 1-octin-8-yl, 1-nonin-9-yl, 1-decin-10-yl or 1-dodecin-12-yl.

$C_7$-$C_{12}$Aralkyl is, for example, benzyl, 2-benzyl-2-propyl, 6-phenyl-ethyl, 9-fluorenyl, α,α-dimethylbenzyl, ω-phenyl-butyl, ω-phenyl-pentyl or ω-phenyl-hexyl. When $C_7$-$C_{12}$aralkyl is substituted, either the alkyl moiety or the aryl moiety of the aralkyl group can be substituted.

$C_6$-$C_{12}$Aryl is, for example, phenyl, naphthyl or 1-biphenyl.

Halogen is for example F, Cl, Br or J, preferably F on alkyl and Cl or Br on aryl.

$C_1$-$C_{11}$Heteroaryl is an unsaturated or aromatic radical having 4n+2 conjugated π-electrons, for example 2-thienyl, 2-furyl, 1-pyrazolyl, 2-pyridyl, 2-thiazolyl, 2-oxazolyl, 2-imidazolyl, isothiazolyl, triazolyl, tetrazolyl or any other ring system consisting of thiophene, furan, thiazole, oxazole, imidazole, isothiazole, thiadiazole, triazole, pyridine, pyrazine, pyrimidine, pyridazine and benzene rings and unsubstituted or substituted by from 1 to 6 ethyl substituents.

Heterocyclic groups are for example

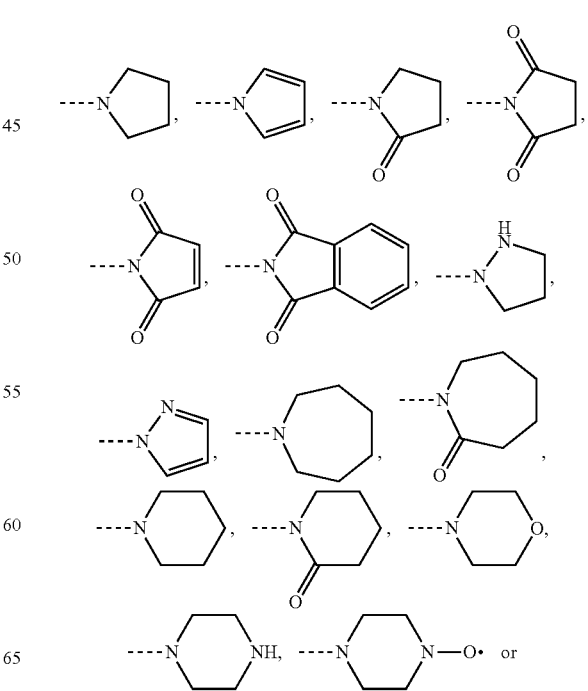

-continued

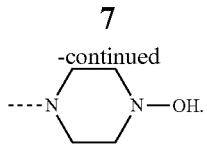

Heterocyclic groups may also be formed by linking adjacent substituents of aryl, for example

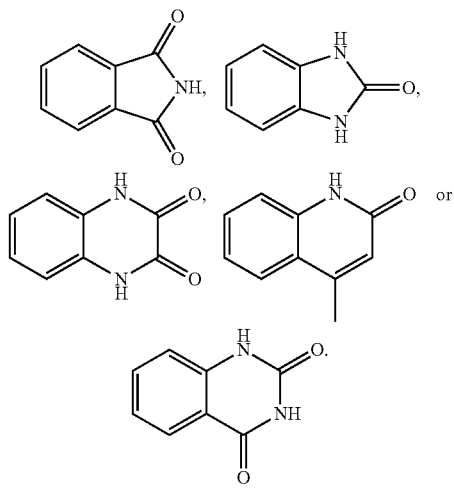

Preferred colourants are the pigment of the formula 1

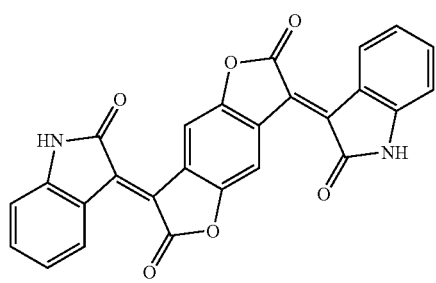

and the novel sulfonic acid of the formula 2a

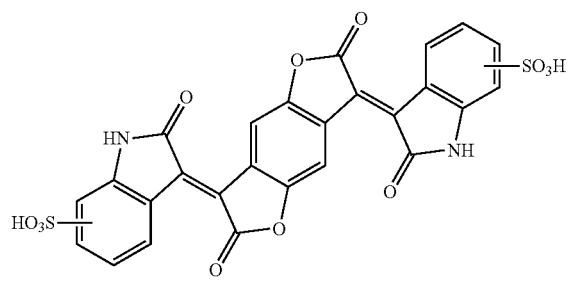

or a salt thereof and/or a cis/trans-isomer of said acid or salt.

The invention relates also to said novel novel sulfonic acid of the formula 2a or a salt thereof and/or a cis/trans-isomer of said acid or salt.

The bis-oxodihydroindolylen-benzodifuranone colourants of the present invention are prepared e.g. as described in WO00/24736 A1, especially according or in analogy to the method disclosed in example 12b of WO00/24736 A1. Novel colourants of the formula I described in the present patent application carrying a sulfonic acid group or isomers or tautomers thereof can be also prepared by reaction of the compound disclosed in example 12b of WO00/24736 A1 with fuming sulfuric acid.

Specific Dispersants

Said specific dispersants are polymers or copolymers, preferably modified polyacrylate or polymethacrylate polymers, especially block copolymers comprising modified polyacrylate or polymethacrylate polymers, obtainable by the process described in WO 2006/074969 A1 (which is incorporated herein by reference) comprising the steps a1) polymerizing in a first step one or more ethylenically unsaturated monomers in the presence of at least one nitroxylether having the structural element of the formula

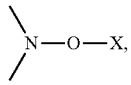

wherein X represents a group having at least one carbon atom and is such that the free radical X. derived from X is capable of initiating polymerization; or a2) polymerizing in a first step one or more ethylenically unsaturated monomers in the presence of at least one stable free nitroxyl radical of the formula

and a free radical initiator; wherein at least one monomer used in the steps a1) or a2) is a $C_1$-$C_6$ alkyl or hydroxy $C_1$-$C_6$ alkyl ester of acrylic or methacrylic acid; and a second step b) comprising the modification of the polymer or copolymer prepared under a1) or a2) by a transesterification reaction, an amidation, hydrolysis or anhydride modification or a combination thereof.

For the reasons stated on pages 2 and 3 of WO 2006/074969 A1 the dispersants obtainable by the above process (which employs a post-polymerisation modification technique) differ distinctly in structural respect from polymers with same monomer composition, but synthesized directly from corresponding monomers without post-modification. It should especially be noted that the monomer distribution which results from the transesterification step, is only governed by the transesterification reaction and can be expected to provide a more uniform i.e. random distribution along the polymer chain, as compared to direct synthesis by radical polymerisation.

The ethylenically unsaturated monomer in step a1 or a2 is preferably selected from isoprene, 1,3-butadiene, α-$C_5$-$C_{18}$alkene, 4-vinyl-pyridine or pyridinium-ion, 2-vinyl-pyridine or pyridinium-ion, vinyl-imidazole or imidazolinium-ion, dimethylacrylamide, 3-dimethylamino-propylmethacrylamide, styrene, α-methyl styrene, p-methyl styrene, p-tert-butyl-styrene or a compound of formula $CH_2$=$C(R_a)$—(C=Z)—$R_b$, wherein $R_a$ is hydrogen or methyl, $R_b$ is $NH_2$, $O^-$ $(Me^+)$, unsubstituted $C_1$-$C_{18}$alkoxy, $C_2$-$C_{100}$alkoxy interrupted by at least one N and/or O atom, or hydroxy-substituted $C_1$-$C_{18}$alkoxy, unsubstituted $C_1$-$C_{18}$alkylamino, di($C_1$-$C_{18}$alkyl)-amino, hydroxy-substituted $C_1$-$C_{18}$alkylamino or hydroxy-substituted di($C_1$-$C_{18}$alkyl)amino, —O—$CH_2$—$CH_2$—N($CH_3$)$_2$or —O—$CH_2$—$CH_2$—$N^+H(CH_3)_2$An$^-$;

An$^-$ is a anion of a monovalent organic or inorganic acid;

Me is a monovalent metal atom or the ammonium ion;

Z is oxygen or sulfur; with the proviso that, as stated above, at least one monomer used in the steps a1) or a2) is a $C_1$-$C_6$ alkyl or hydroxy $C_1$-$C_6$ alkyl ester of acrylic or methacrylic acid.

A nitroxylether having the structural element of the formula

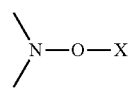

is e.g. a compound of the formula

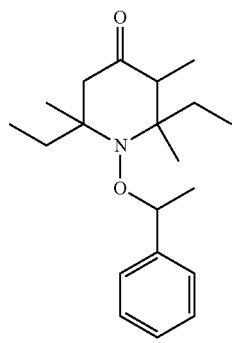 [SMILES: CCC1(C)CC(=O)C(C)C(C)(CC)N1OC(C)c1ccccc1]

Stable free radicals having a structural element

are for example disclosed in EP-A-621 878 (Xerox).

Examples, such as

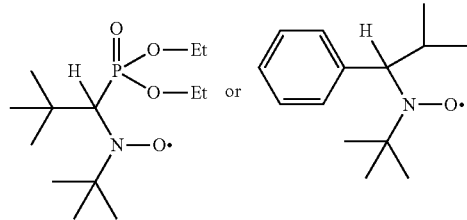

are given in WO96/24620 (Atochem).

Particularly suitable nitroxylethers and nitroxyl radicals are those of formulae

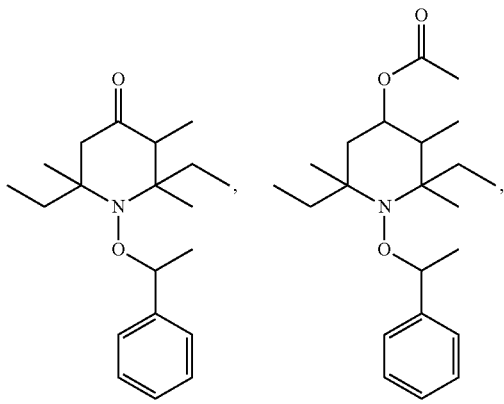

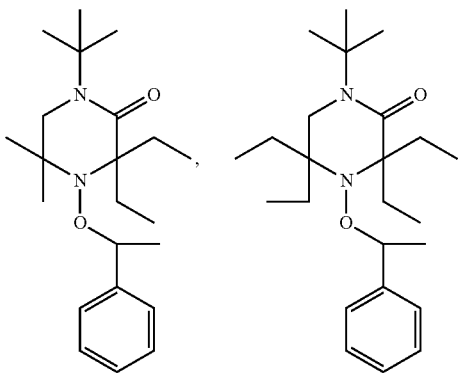

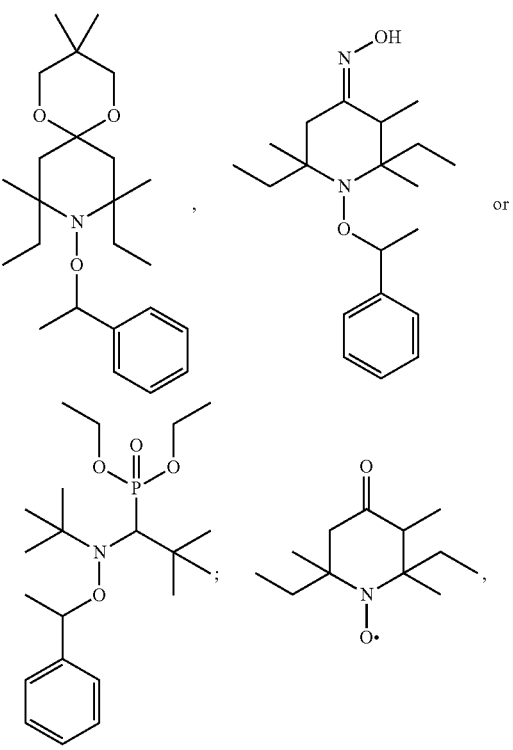

or

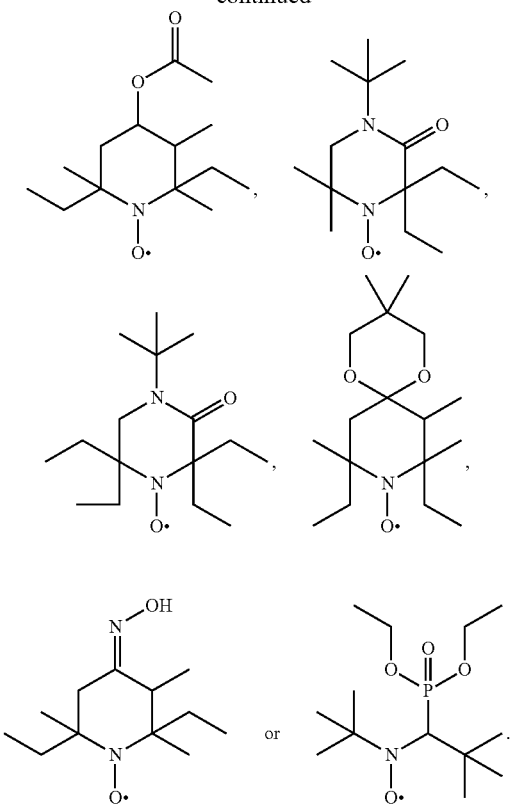

When the process according to route a2) is chosen, the free radical initiator is preferably an azo compound (e.g. 2,2'-azobisisobutyronitrile), a peroxide (e.g. acetyl cyclohexane sulphonyl peroxide), perester (e.g. disuccinic acid peroxide) or a hydroperoxide (e.g. t-butyl hydroperoxide).

Preferably the first polymerization step is carried out according to the polymerization reactions a1).

Preferably the second step b) is a transesterification reaction, hydrolysis or an anhydride modification. Particularly preferred is a transesterification reaction.

The transesterification preferably comprises the removal of the $C_1$-$C_6$ alcohol byproduct by distillation.

In a specific embodiment step a1 or a2 of the above described process is carried out twice and a block copolymer is obtained wherein in the first or second radical polymerization step the monomer or monomer mixture contains 50 to 100% by weight, based on total monomers, of a $C_1$-$C_6$ alkyl or hydroxyalkyl ester of acrylic or methacrylic acid and in the second or first radical polymerization step respectively, the ethylenically unsaturated monomer contains no primary or secondary ester bond.

When a block copolymer is prepared it is preferred that in the first polymerization step the monomer or monomer mixture contains from 50 to 100% by weight based on total monomers of a $C_1$-$C_6$ alkyl or hydroxyalkyl ester of acrylic or methacrylic acid and in the second polymerization step the ethylenically unsaturated monomer is 4-vinyl-pyridine or pyridinium-ion, 2-vinyl-pyridine or pyridinium-ion, vinyl-imidazole or imidazolinium-ion, dimethylacrylamide, 3-dimethylaminopropylmethacrylamide, styrene, α-methyl styrene, p-methyl styrene or p-tert-butyl-styrene.

In a specific embodiment of the invention the block copolymer is a gradient block copolymer.

As mentioned above it is mandatory that the polymer or copolymer is prepared by controlled free radical polymerization (CFRP). Solomon et al. in U.S. Pat. No. 4,581,429 have firstly described such processes using stable free nitroxyl radicals as controlling agents. These are the steps defined under a1) and a2) above.

U.S. Pat. No. 4,581,429 discloses a free radical polymerization process by controlled or "living" growth of polymer chains, which produces defined oligomeric homopolymers and copolymers, including block and graft copolymers. Disclosed is the use of initiators of the partial formula R'R"N—O—X. In the polymerization process the free radical species R'R"N—O. and .X are generated. .X is a free radical group, e.g. a tert.-butyl or cyanoisopropyl radical, capable of polymerizing monomer units containing ethylene groups.

As stated above, reaction step b) comprises the modification of the polymer or copolymer prepared by reaction steps a1) or a2) by a transesterification reaction, an amidation, hydrolysis or anhydride modification or a combination thereof.

Transesterification means to replace the alcohol radical in an ester group of the polymer or copolymer by another alcohol radical. Preferably the alcohol radical to be replaced is methanol, ethanol, propanol or butanol. Typically the transesterification reaction is carried out at elevated temperatures, typically 70-200° C., by reacting the CFRP polymer with the corresponding alcohol using well-known catalysts, such as tetra-isopropyltitanate, tetra-butyltitanate, or alkali- or earth alkali alcoholates, like NaOMe, LiOMe or LiOC(CH$_3$)$_3$. Typically the low boiling product alcohol is removed from the transterification reaction mixture by distillation. If needed, catalyst residues may be removed by adsorption or extraction or otherwise processed or inactivated by known methods, like hydrolysis with water or acids. The choice of the replacing alcohol is important. The replacing alcohol controls the properties of the resulting copolymer.

Hydrolysis means the cleavage of an ester bond under alkaline or acidic conditions and can be carried out when the polymer or copolymer contains ester functionalities. The degree of hydrolysis may vary in a wide range and depends on reaction time and conditions. For example 5 to 100%, preferably 10% to 70% of the ester functionalities may be hydrolized, to form the free acid group, from which also a salt can be prepared. The metal ion is preferably an alkali metal ion, such as $Li^+$, $Na^+$ or $Ka^+$ or an ammonium cation, such as $NH_4^+$ or $NR_4^+$, wherein R is hydrogen or $C_1$-$C_{18}$alkyl with the proviso that the four R need not all have the same meaning.

Anhydride modification can be carried out when the polymer or copolymer contains hydroxyl functionalities. The hydroxyl functionalities come for example from hydroxyl functional monomers, such as hydroxyethyl acrylate or methacrylate. Virtually all aliphatic or aromatic anhydrides can be used in the modification process. Examples for anhydrides are maleic acid anhydride, pyromelitic acid anhydride, cyclohexyldiacid anhydride, succinic acid anhydride, camphoric acid anhydride.

Preferably, the dispersants are polymeric dispersants selected from modified poly(meth)acrylate polymers of the formula II

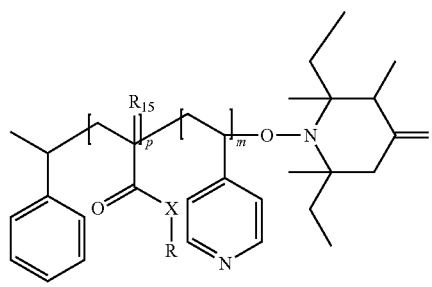

wherein X represents oxygen or the group NH, m is 0 or 10-20, p is 60-90, $R_{15}$ is hydrogen or methyl, and R represents alkyl having up to 30, preferably up to 20, more preferably up to 16 carbon atoms wherein one or more carbon atoms may be replaced by oxygen and which is unsubstituted or substituted by dimethylamino or trimethylamino with the proviso that the group X—R is not the same in all (p) moieties of the partial formula —CH$_2$—C(R$_{15}$)(CO—X—R)— present in formula I and the different groups X—R are randomly distributed along the polymer chain, and salts of such polymers having a salt-forming group.

When m is 0 the pyridyl-ethylene moiety is absent.

Alkyl R having up to 30 carbon atoms wherein one or more carbon atoms are replaced by oxygen and which is substituted by dimethylamino or trimethylamino is e.g. 5-dimethylamino-3-oxapentyl of the formula (CH$_3$)$_2$N—CH$_2$—CH$_2$—O—CH$_2$—CH$_2$— or 5-trimethylamonio-3-oxapentyl, and is preferably different from 2-dimethylaminoethyl.

Preferably, alkyl R has 2-20, especially 4-16 carbon atoms and is e.g. n-butyl or linear or branched C$_{12-16}$alkyl, like 1-hexadecyl.

As stated above the group X—R must not be the same in all (p) moieties of the partial formula —CH$_2$—C(R$_{15}$)(CO—X—R)— present in formula I. Preferably, in up to 20% of said moieties R is unsubstituted C$_{1-6}$alkyl, e.g. 1-butyl, while in the remaining moieties R is different from unsubstituted C$_{1-6}$alkyl, e.g. linear or branched C$_{12-16}$alkyl, like 1-hexadecyl, or 5-dimethyl-amino-3-oxapentyl of the formula (CH$_3$)$_2$N—CH$_2$—CH$_2$—O—CH$_2$—CH$_2$— or 5-trimethylamonio-3-oxapentyl.

A salt-forming group in a compound of the formula I is especially a dimethylamino group which may be reacted e.g. with methyliodide to form a trimethylamonio group. Suitable counterions are e.g. tetraphenyl-borate or a dialkylphosphonate, like didodecylphosphonate.

Solvents for the Dispersions

Examples of suitable solvents for dispersants are aliphatic hydrocarbons, e.g. the high-purity isoparaffinic solvents with narrow boiling ranges Isopar™ G and Isopar™ M; halogenated hydrocarbons, like tetrachloroethylene and Halocarbon™ 0.8 (a low molecular weight polymer of chlorotrifluoroethylene), and silicone fluids. A preferred dispersant is dodecane.

The dispersions of the present invention can be used in electrophoretic displays.

The invention relates also to the use in an electrophoretic display of a bis-oxodihydro-indolylene-benzodifuranone colourant of the formula I, and/or of a polymeric dispersant as defined herein, and to the use in an electrophoretic display of a dispersion comprising a bis-oxodihydro-indolylene-benzodifuranone colourant of the formula I, a polymeric dispersant as defined herein, and a suitable solvent.

The invention relates also to an electrophoretic display comprising a dispersion of a bis-oxodihydro-indolylene-benzodifuranone colourant of the formula I, a polymeric dispersant as defined herein and a solvent which is suitable for dispersions used in electrophoretic displays.

The following Examples illustrate the invention.

EXAMPLES

Abbreviations:
DMAPMA: N,N-Dimethylaminopropyl methacrylamide
DMAEE: Dimethylaminoethoxyethanol
hyflo: Hyflo SuperCel® (Fisher Scientific, Inc.); flux calcined diatomaceous earth
GPC: gel permeation chromatography
LDI-TOF MS: Laser desorption/ionization time-of-flight mass spectrometry
$M_n$: Number average molecular weight
nBA: n-butylacrylate
PDI: Polydispersity (The polydispersity of a sample is defined as weight average molecular weight $M_w$ divided by $M_n$ and gives an indication just how narrow a distribution is.)
Ph$_4$BNa: Tetraphenylborane sodium salt
THF: tetrahydrofurane
4VP: 4-vinyl-pyridine Abbreviations for NMR Spectra
s: singulet
t: triplet
m: multiplet Reagents:
Cetylalcohol (98% pure1-hexadecanol; obtainable from the company Cognis)
LIAL® 125 A: mixture of straight chain and mono-branched C$_{12-15}$ alkanols from Sasol Olefins and Surfactants GmbH.
Lupragen® N 107: Dimethylaminoethoxyethanol (obtainable from the company BASF)

General Remarks on the Nomenclature and Formulae Given Herein for Polymeric Dispersants As stated in Example 6 the transesterification proceeds at random. This is not reflected properly by many formulae, like formula 4 according to which it would seem that there is a block of butyl esters and a block of C$_{12-15}$-alkyl esters. Nevertheless, said formulae are more illustrative than e.g. formula 4' and have been used for this reason. In contrast to the formulae, the abbreviated names better reflect which part of the polymer is random and which part is a block. For example the name poly(nBA-co-LialA-b-DMAPMA) given in Example 7 describes a polymer comprising a block (characterized by the letter "b") of poly-n-butylacrylate wherein the butyl group has at random be replaced by LIAL® alcohols, i.e. poly(nBA-coLialA) and another block of poly-dimethylaminopropylmethacrylamide. The approximated numbers of the monomers in said blocks are given e.g. in Example 7 as (11-co-60)-b-10, i.e. there are approximately 11 n-butylacrylate units at random copolymerized with 60 Lial-acrylate units followed by a block of 10 dimethylaminopropylmethacrylamide (DMAPMA) units. It should, however, be noted that the abbreviated names do not mention the end groups on both sides of the polymer, i.e. e.g. the 1-phenyl-ethyl group.

Preparation of Known and Novel Pigments

Example 1

Manufacture of the Pigment of the Formula 1

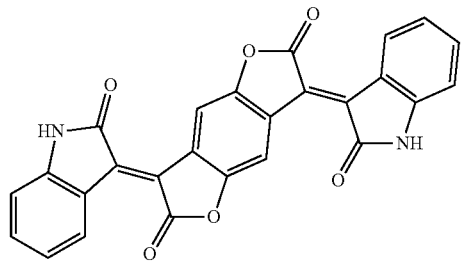

1

The synthesis of the pigment of the above formula 1 from bisbenzofuranone and isatin is described in Example 12b on page 35 of WO 00/24736 A1). The product is described in WO 00/24736 A1 as a "violet powder". While the inventors of the present patent application consider the above formula 1 to represent the most likely structure of the product obtained according to said Example 12b, the structure is not absolutely certain. The correct structure could also correspond to an isomer, especially a cis/trans-isomer of formula 1, or to a mixture of such isomers.

A new synthesis which yields an improved form of the pigment of the above formula 1, a cis/trans-isomer thereof or a mixture of such isomers is described hereinafter:

A mixture of 8.5 g of 2,5-dihydroxy-1,4-benzenediacetic acid (0.37 Mol, Aldrich), 11 g Isatin (0.74 Mol, Aldrich 98%) and 14 g of p-toluenesulfonic acid-monohydrate (Fluka purum) in 800 ml of glacial acetic acid is stirred during 14 hour at 105° C. The reaction mixture is cooled to room temperature and the suspension filtered over a paper filter, washed with 250 ml of acetic acid, 200 ml of methanol and 500 ml of water. The black powder is dried in a vacuum oven at 70° C./104 Pa.

Examples 2 to 5

General Procedure for Examples 2 to 5

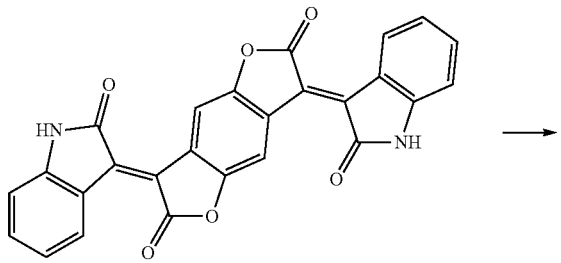

1

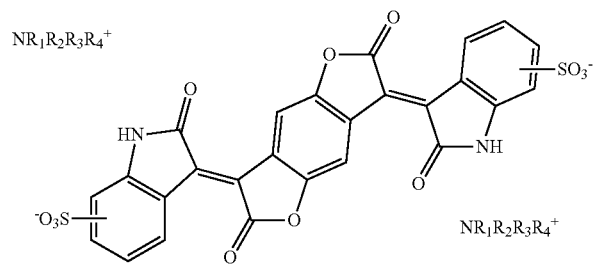

2

$R_1, R_2, R_3$ = alkyl
$R_4$ = H or alkyl

Position o fthe sulfo groups not defined 5.00 g of the black pigment of the above formula 1 or an isomer thereof (obtained by the new synthesis described in Example 1) are dissolved under stirring in 30 ml of fuming sulfuric acid (comprising 25% of free $SO_3$). The dark violet solution, whose temperature has reached 30° C., is cooled down to 20° C., stirred for 4 hours, discharged into 500 ml of an ice/water-mixture and stirred for another hour. 25 g (i.e. a multiple stoichiometric excess) of the amine or ammonium salt specified in Examples 2 to 5 are added within 5 minutes. The black suspension is stirred for 30 minutes, filtered and washed with 50 ml of water. The humid presscake is suspended in 100 ml of water, 5 g of the amine or ammonium salt are added, and the product is extracted twice each with 150 ml of methylene chloride. The two organic phases are merged and stirred into 1200 ml of hexane; the product precipitates as small crystals. The suspension is stirred for 30 minutes and filtered on a fibre glass filter. As the product tends to liquefy on the filter, the product is dissolved off the filter with 100 ml of methylene chloride and isolated by evaporating the solvent on the rotavapor at slightly elevated temperature under vacuum.

The products contain predominantly two sulfo groups, as determined by MS technique. Based on $^1$H-NMR-data the exact location of the sulfo groups is uncertain.

Example 2a:

Manufacture of the Pigment of the Formula 2a

In order to manufacture a disulfonic acid of the formula 2 where the location of the sulfo groups is certain, i.e. as depicted in the below formula 2a, the following process of manufacture is used:

A mixture of 2.3 g of 2,5-dihydroxy-1,4-benzenediacetic acid (0.01 Mol, Aldrich), 5.7 g of isatin-5-sulfonic acid sodium salt dihydrate (0.02 Mol, Fluka 98%) and 0.7 g p-toluene-sulfonic acid-monohydrat (Fluka purum) in 80 ml acetic acid and 20 ml water is stirred during 14 hour at 105° C. The reaction mixture is cooled to 80° C. and the suspension filtered over a paper filter, washed with 80 ml of acetic acid and 100 ml of methanol. The black powder is dried in a vacuum oven at 70° C./10$^4$Pa (Pa=Pascal) yielding the compound of formula 2a ; LDI-TOF: m/z=608.

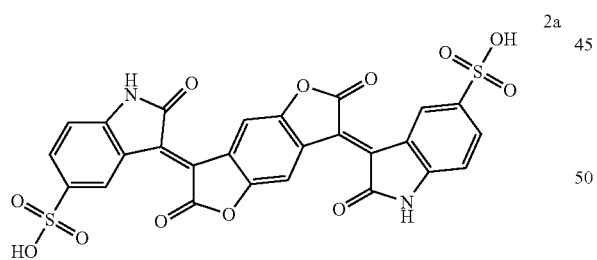

2a

Example 2

Tributylammonium salt of the above formula 2; used amine: tributylamine. Yield: 2.1 g Example 3

Trioctylmethylammonium salt of the above formula 2; used ammonium salt: trioctylmethylammonium bromide. Yield: 1.6 g The product is characterized by elemental analysis, corresponding to the bis(trioctylmethylammonium) salt:

Found (Calculated): C, 66.35% (67.92%); H, 9.02% (8.85%); N, 3.86% (4.17%); O, 14.25% (14.29%); S, 5.44% (4.77%). No residual bromide is detected.

Example 4

Octadecyltrimethylammonium salt of the above formula 2; used ammonium salt: octadecyltrimethylammonium bromide. Yield: 8.3 g The product is characterized by elemental analysis, corresponding to the mono(octadecyltrimethylammonium) salt monohydrate:

Found (Calculated): C, 59.06% (60.18%); H, 7.46% (6.34%); N, 4.01% (4.48%); O, 21.25% (22.17%); S, 6.78% (6.84%). No residual bromide is detected.

Example 5

Tetraethylammonium salt of the above formula 2; used ammonium salt: tetraethylammonium bromide. Yield: 1.2 g Preparation of Reagents and Copolymers Used as Dispersants Example 6

Synthesis of Compound 4 (4 '), i.e. poly(nBA-co-CetylA-b-4VP)

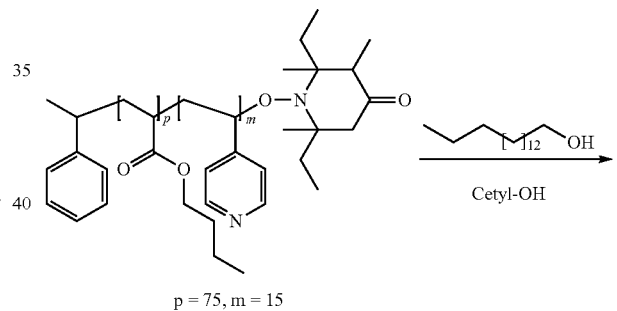

p = 75, m = 15

3

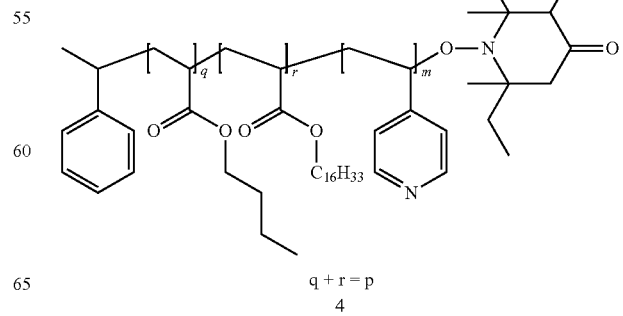

q + r = p

4

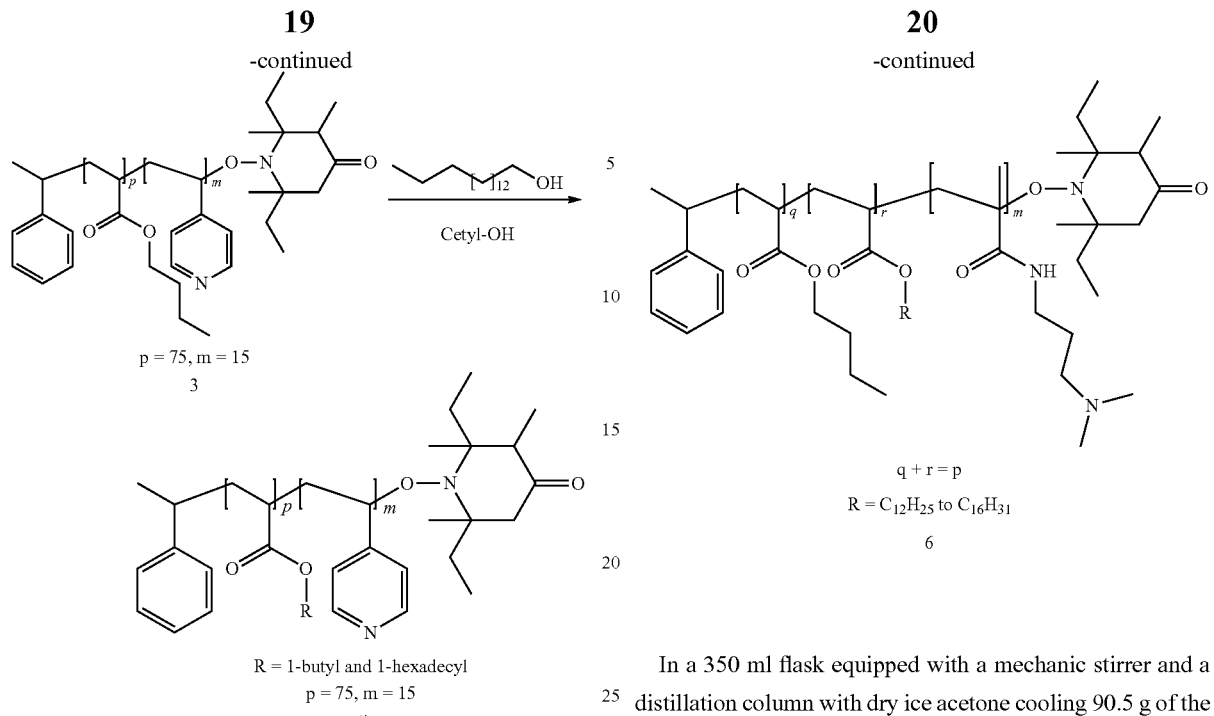

R = 1-butyl and 1-hexadecyl
p = 75, m = 15
4'

In a 500 mL flask equipped with a mechanical stirrer and a distillation column with dry ice acetone cooling, 100.0 g of poly(nBA-b-4VP), i.e. a block copolymer of n-butylacrylate and 4-vinylpyridine, degree of polymerization 75-b-15, described in example A2 on page 36 of WO2006/074969 A1, 100 g of xylene and 71.7 g of cetylalcohol (molecular weight 242.5 g/mol; 45 mol % relative to the n-butyl esters) are added and dried by azeotropic distillation of the xylene. Three portions of 0.25 g of tert. butoxylithium (LiO$^t$Bu) are added during 5 h at 190° C. The formed n-butanol is distilled off at reduced pressure. As a result, 149.8 g of poly(nBA-co-CetylA-b-4VP) of the formula 4 are obtained as a yellowish wax. Number average molecular weight $M_n$=15.400 g/mol (PDI 1.5). Analysis via gel permeation chromatography (GPC) as well as $^1$H-NMR indicate almost quantitative conversion of the cetylalcohol.

The above formula 4 does probably not reflect the structure of the obtained product correctly in that the transesterification probably proceeds at random so that the true structure of the obtained product seems to be better reflected by formula 4'. Analogous comments apply to the below Examples 7 to 9.

Example 7
Synthesis of poly(nBA-co-LialA-b-DMAPMA) of Formula 6

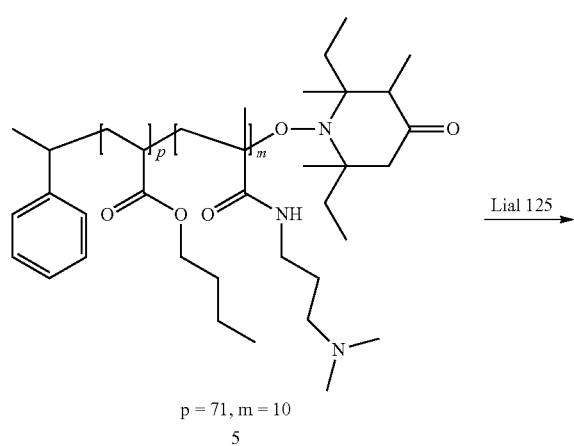

p = 71, m = 10
5

In a 350 ml flask equipped with a mechanic stirrer and a distillation column with dry ice acetone cooling 90.5 g of the copolymer of formula 5 and 100.3 g of Lial 125 (80 mol % relative to the n-butyl esters) are placed and inertisized by bubbling nitrogen through the solution during 1 hour at room temperature. The mixture is heated to 135-142° C. and catalyst is added (4 portions of 350 mg of tetra(isopropyl)orthotitanate, each 2 hours). The formed n-butanol is distilled off at low pressure (200 mbar). After 8 hours the resulting brownish polymer is cooled to room temperature, affording 145.1 g of the copolymer of the formula 6 ($M_n$ 11300, PDI 1.35 (by GPC (THF)), solid content 97.3% (halogen dryer 200° C.) and a composition (according to $^1$H-NMR) for poly(nBA-co-LialA-b-DMAPMA) as (11-co-60)-b-10.

The starting material of the formula 5 is obtained as follows:

Step 7.1

In a 500 ml flask, equipped with a mechanic stirrer and distillation column are loaded 122.5 g of poly-n-butylacrylate [poly(nBA)] (synthesized analogous to Example A1 in WO2006/074969; degree of polymerization 75 according to $^1$H-NMR, $M_n$=6830, PDI=1.31 and 85.98 g of dimethylaminopropyl methacrylamide (DMAPMA). The mixture is heated under nitrogen to 135° C. After 2.5 h the reaction is terminated by cooling below 100° C. and non-reacted monomer DMAPMA is distilled off at high vacuum (<20 mbar) until a solid content of >98.0% is reached (by halogen dryer 200° C.).

As a result, 143 g of the brownish viscous block copolymer of the formula 5 are isolated with $M_n$[GPC (THF)] 7480, (PDI 1.32). According to analysis by $^1$H-NMR the degree of polymerization is determined for p(nBA-b-DMAPMA) as 71-b-10.

Example 8

Synthesis of the Copolymeric Salt of the Formula 7 [poly(nBa-co-LialA-co-DMAEE[Me-quat]A-b-DMAPMA)]$^+$(TPB)$^-$

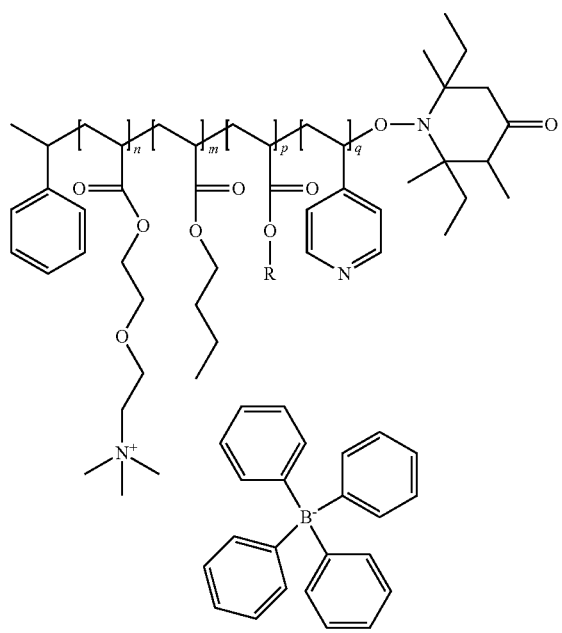

7

R = C$_{12}$H$_{25}$ to C$_{15}$H$_{31}$

In a 500 mL flask equipped with a mechanic stirrer and a distillation column with dry ice acetone cooling 200.0 g of poly(nBA-b-4VP) of the formula 3 depicted in Example 6 with a degree of polymerization of 75-b-15, prepared according to example A2 in WO2006/074969, 203.1 g of Lial 125 (ca. 100 mol % relative to the n-butyl esters) and 4.6 g of Lupragen N 107 (MW 133.2, ca. 3 mol % relative to the n-butyl esters; dimethylaminoethoxyethanol [DMAEE]) are added. One portion of 2.5 g of tetra(isopropyl)orthotitanate is added and the mixture is stirred under inert conditions and low pressure for 8 hours at 140° C., distilling off formed n-butanol. At the end of the process, residual excess alcohols are removed under high vacuum (20 mbar) until solid content of >95% (halogen dryer, 200° C.) is reached. This affords a brownish viscous polymer with the average ($^1$H-NMR) composition for p(nBA-co-DMAEEA-co-Lial125A)-b-p(4VP) as (5-co-1-co-70)-b-15 and a M$_n$(GPC/THF) of 17.500 (PDI 1.31). 50.0 g of this polymer are placed in a 250 ml three necked flask, equipped with a mechanical stirrer, and 100 g of n-dodecane are added. The mixture is slightly heated to 40° C. to obtain a homogenous solution. After cooling to room temperature, 0.29 g of methyliodide (1.0 equiv relative to aminogroups) are added to the polymer solution and subsequently stirred overnight at room temperature. The resulting quaternized polymer solution is obtained with a solid content of 32.1% (halogen dryer, 200° C.) and a M$_n$(GPC/THF) of the polymer of 14.300 (PDI 1.29). In the final step, 0.66 g of sodium tetraphenylborate (Ph$_4$BNa), dissolved in 13.2 g of dodecane, are slowly added to the polymer solution and stirred for 3 hours at room temperature. The resulting slightly turbid mixture is filtered over hyflo resulting in a yellowish solution (solid content 31.3%) and a M$_n$of 14.300 (PDI 1.24) of the salt of the formula 7. The average ($^1$H-NMR) composition of the cation is determined for p(nBA-co-DMAEE[Me-quat]A-co-Lial125A)-b-p(4VP)$^+$ as (5-co-1-co-70)-b-15.

Example 9

Synthesis of the Dispersant of Formula 9 [poly(nBA-co-LialA-co-DMAEE[H]A)-b-DMAPMA]$^+$ (DDDP)$^-$

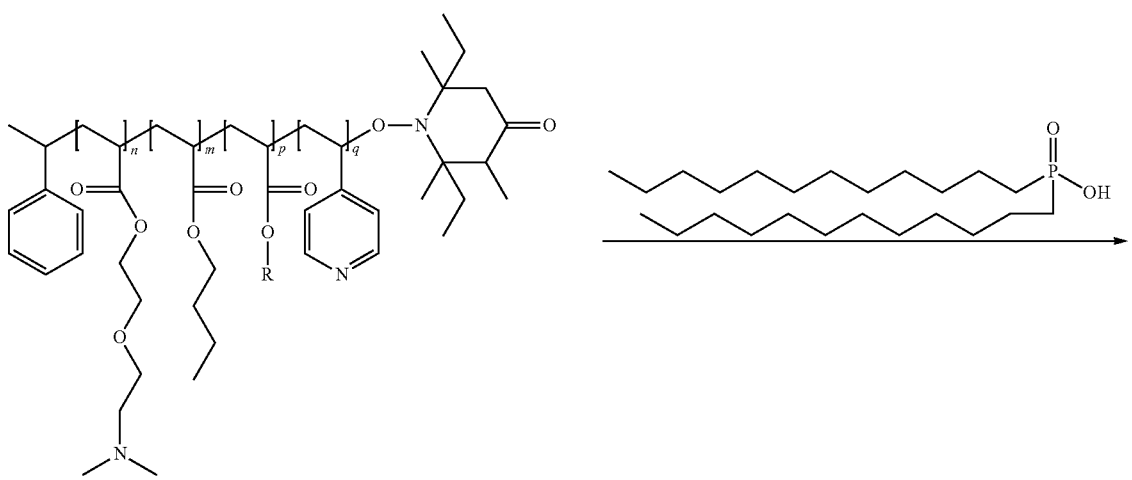

n = 1 m = 7 p = 66 q = 14
R = C$_{12}$H$_{25}$ to C$_{15}$H$_{31}$

-continued

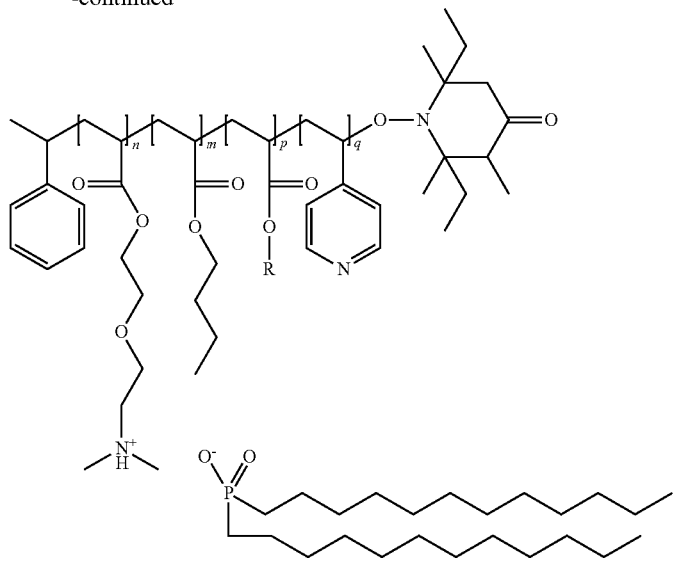

9

50.0 g of the copolymer of formula 8 are homogenously dissolved in 283 g of n-dodecane at 50° C. The didodecylphosphonate (DDDP, 0.64 g) of the formula 10 described in step 9.2 is added and stirred for 2 hours at 80° C. The ammonium salt of the formula 9 is obtained as a clear brownish solution in n-dodecane. GPC(THF) of the polymer gives a $M_n$ of 18.800 (PDI 1.30). The average ($^1$H-NMR) composition of the cation p(nBA-co-DMAEE[H]A-co-Lial125A)-b-p(4VP)$^+$ is determined to be (7-co-1-co-66)-b-14.

The starting materials are prepared as follows:
Step 9.1: Synthesis of the Copolymer of the Formula 8

In a 500 mL flask equipped with a mechanic stirrer and a distillation column with dry ice acetone cooling, 175 g of the copolymer of the formula 8 are prepared according to the procedure of Example 8: 103.7 g of a p(nBA)-b-p(4VP) block copolymer with an average ($^1$H-NMR) composition of 73 nBA and 14 4-vinylpyridine units, 110.1 g of Lial 125 (ca. 100 mol % relative to n-butylesters), 1.0 g of Lupragen N 107 (MW 133.2; 1.5 mol % relative to the n-butyl esters) and 1.3 g of tetra(isopropyl)orthotitanate are transesterified (18 hours at 140° C. and 200 mbar) to a brownish viscous copolymer of the formula 8 with the average ($^1$H-NMR) composition for p(nBA-co-DMAEEA-co-Lial125A)-b-p(4VP) of (7-co-1-co-66)-b-14 and a $M_n$(GPC/THF) of 15.900 (PDI 1.61).

Step 9.2; Synthesis of Didodecylphosphonate (DDDP) of the Formula 10

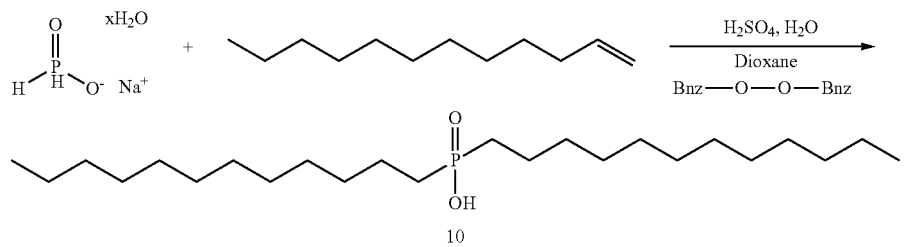

10

In a 250 ml three necked flask, equipped with a magnetic stirring bar, 10.6 g of sodium hypophosphite monohydrate (Fluka, MW 106) are dissolved in 10 ml of water and cooled to 15° C. To this solution 7.51 g of concentrated sulfuric acid (97%, 0.75 equivalents) are slowly introduced, resulting in a turbid viscous reaction mass. 35.4 g of 1-dodecene (2.0 equivalents) are added at room temperature, followed by a solution of 2.42 g of dibenzoyl peroxide (Bnz-O—O-Bnz; Fluka; 50% in water) in 20 ml of 1,4-dioxane. The inhomogeneous mixture is heated to 80-85° C. and stirred for 2 hours, followed by another portion of 2.42 g of dibenzoyl peroxide (Fluka, 50% in water) in 20 ml of 1,4-dioxane and stirring for 2 hours at 85° C. After cooling to room temperature, 50 ml of toluene are added, heated to 60° C., and cooled to room temperature. The two phase system is seperated and the aquous phase is extracted two times with each 50 ml of toluene. The combined organic phases are washed with water and a nearly saturated aqueous sodium chloride solution (brine; 2 times 20 ml and 1 time 20 ml respectively). After filtration over hyflo, the toluene is evaporated to dryness. The residual solid is dissolved in hot hexane (60° C., 200 ml) and left to cool down for crystallization. Part of the crystals are filtered off, the filter cake is washed with cold hexane, and dryed at 25° C. on a rotorvap. This affords 14.65 g (36% yield) of the compound of the formula 10 as a white crystalline material; $^1$H-NMR (CDCl3, ppm): 9.8 (s, 1H, OH); 1.5-1.8 (m, 8H, 2 P—$CH_2$—$CH_2$—)), 1.2-1.5 (m, 36H, 18-$CH_2$—), 0.9 (t, 6H, 2 $CH_3$).

Example 10

Synthesis of poly(nBA-co-LialA-b-4VP) of the Formula 11

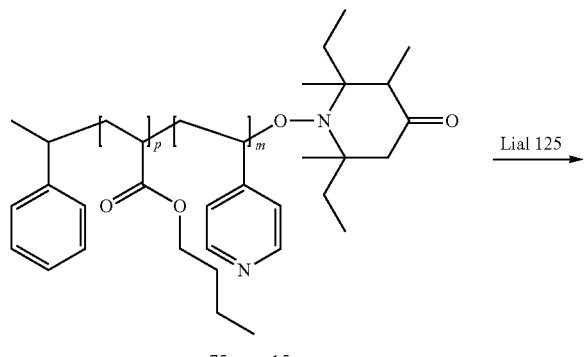

p = 75, m = 15

3

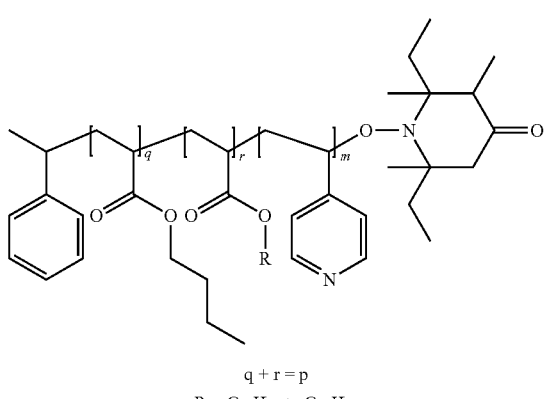

q + r = p
R = $C_{12}H_{25}$ to $C_{15}H_{31}$

11

In a 100 mL flask equipped with a mechanical stirrer, distillation column with dry ice acetone cooling, 18.77 g of poly(nBA-b-4VP), degree of polymerization 73-b-14, prepared according to example A2 in WO2006/074969, and 20.63 g of Lial-125 (80 mol % relative to the n-butyl esters) are added and degassed at 65° C. for 60 minutes at 50 mbar. Three portions of 0.29 g of titanium-bis(acetylacetonate)-bis-isopropylate are added during 6 hours at 142° C. The formed n-butanol is distilled off at reduced pressure.

As a result, 28.94 g of the copolymer of the formula 11 [poly(nBA-co-LialA-b-4VP)] are obtained as a brownish viscous substance; $M_n$=18.760 g/mol (PDI 1.34). Analysis via GPC as well as $^1$H-NMR indicate almost quantitative conversion of the Lial-125 alcohol.

Example 11

Preparation and Characterization of Dispersions

This example illustrates the preparation of the oil phase containing various dispersed electrophoretic black pigment particles. The physical characteristics of the obtained dispersions are given in Table 1 below.

General Procedure for the Preparation of the Dispersions:

1.00 g of the pigment substance is milled by a disperser DAS 200 (Lau GmbH) for 15 hours at 25° C. into 9.0 g of dodecane (749.0 kg/m$^3$) (Aldrich D22, 110-4) in the presence of 0.75 g of the dispersant mentioned in Table 1. In the case of the two-colour electrophoretic dispersion of Example 11i the above-mentioned 1.00 g of the pigment substance are replaced by 0.5 g of each of the pigments mentioned in Example 11i.

The dispersion is diluted with further dodecane from 10% to 2% by weight. 20 μl of this dispersion are further diluted with dodecane to 1 ml before measurements by dynamic light scattering.

The size [diameter in nm] and the zeta potential (ξ) [mV] of the dispersed pigment particles are measured by dynamic light scattering by means of a Malvern Zetasizer Nano Series apparatus (Malvern Instruments Ltd., United Kingdom). The resulting particle sizes are shown in the row "Size" of the below Table 1 in units of nanometers, the (calculated) electrophoretic mobilities in the row p in units of 10$^{-8}$ m$^2$/Vs at 40V (the electrophoretic mobility is the coefficient of proportionality between particle speed and electric field strength), and the zeta potential in the row "Zeta (mV)".

The electrophoretic mobility μ [is calculated from the Smoluchowski relation (ξ=μη/∈ where μ is the mobility, η=1.344 mPa*s is the viscosity of the medium at 25° C. and ∈=2.0 is the dielectric constant at 20° C.).

Measurement of the Resistance R

The resistance R [Ω] given in Table 1 is measured as follows:

A dispersion of carbon black (Base Carbon Black from the Cabot Modified Carbon Black Toolkit; Cabot Corp.) in dodecane is prepared as reference, using copolymer 4 (cf. Example 6) SP-10515 as dispersant, according to the above "General Procedure for the Preparation of the Dispersions".

Pure dodecane, the dispersion of carbon black, and the dispersion of pigments (all in a concentration of 2% by weight) are applied in identical volumes into wells of a 96-well-plate from Gatlik Ltd. (Basel, Switzerland; http://www.gatlik.com/) with a three-point electrode geometry for low conductivity, as described in WO 2005/105292 A1 (cf. FIG. 1 thereof). The plates are made of polyimide with flat gold electrodes in a double half-circle arrangement as illustrated in FIG. 1 of the present patent application for one particular well. The wells have a diameter of 5 mm and a depth of 2 mm. Before the measurements, the plate is cleansed with ethanol until the resistance between the electrodes is more than 10$^{13}$Ω. The resistance is measured between the half-circle electrodes, the center electrode serving for grounding. For each sample of dispersion, measurements in three different wells are performed, and the highest and the lowest value excluded.

TABLE 1

| Example | Pigment [formula no./Example] | Dispersant [formula no./Example] | Conc.** | Size [nm] | $\mu$ [$10^{-8}$ m$^2$/Vs at 40 V] | Zeta [mV] | R [$\Omega$] |
|---|---|---|---|---|---|---|---|
| 11a | Carbon Black* | 4/6 | 150 | 149 | $-3.4 \times 10^{-3}$ | $-3.96$ | $3.53 \times 10^9$ |
| 11b | 2/4 | 4/6 | 100 | 551 | $-2.32 \times 10^{-2}$ | $-27.1$ | $5.71 \times 10^9$ |
| 11c | 2a (free disulfonic acid)/2a | 6/7 | 75 | 314 | $-3.09 \times 10^{-2}$ | $-36.1$ | $1.09 \times 10^{10}$ |
| 11d | 2a (free disulfonic acid)/2a | 11/10 | 75 | 338 | $-3.71 \times 10^{-2}$ | $-43.2$ | $4.36 \times 10^{10}$ |
| 11e | 1/1 | 8/9.1 | 75 | 511 | $-1.32 \times 10^{-2}$ | $-15.4$ | $4.69 \times 10^9$ |
| 11f | 1/1 | 4/6 | 75 | 471 | $-1.99 \times 10^{-2}$ | $-23.2$ | Not measured |
| 11g | 1/1 | 9/9 | 75 | 435 | $-2.59 \times 10^{-2}$ | $-30.2$ | Not measured |
| 11h | 1/1 | 7/8 | 75 | 411 | $2.29 \times 10^{-2}$ | $-26.6$ | Not measured |
| 11i | 1/1 + Pigment Yellow 128*** | 6/7 | 75 | 493 | $-1.95 \times 10^{-2}$ | $-22.7$ | Not measured |

*Base Carbon Black from the Cabot Modified Carbon Black Toolkit; Cabot Corp.
**The row "conc." gives the percentage of weight of dispersant relative to the weight of pigment.
***CROMOPHTAL Jet Yellow 8GT; Ciba, Inc.

The resistance of the well with pure dodecane is $>10^{13}\Omega$ ($>10^{13}$Ohm).

As can be seen from Table 1, in all cases the absolute value of the zeta potential and the resistance of the dispersions of the black pigments which are matter of this patent application (Examples 11b to 11e) is higher than that of the reference material carbon black (Example 11a).

The significance of zeta potential is that its absolute (i.e. positive or negative) value is related to the stability of colloidal dispersions. The zeta potential indicates the degree of repulsion between adjacent, similarly charged particles in a dispersion. For molecules and particles that are small enough, like the nano particles of the present invention, a high zeta potential confers stability, i.e. the dispersion resists aggregation. When the potential is low, attraction exceeds repulsion and the dispersion will break and flocculate. So, colloids with high zeta potential (negative or positive) are electrically stabilized while colloids with low zeta potentials tend to coagulate or flocculate. The other importance of the zeta potential is that the mobility of a particle under influence of an electric field is proportional to the zeta potential. The higher the (absolute) zeta potential, the faster is the movement of the particles and the switching between the two states.

A high resistance (resistivity) of the dispersion is desired in order to reduce its electrical conductivity, to get lower power consumption of the display, and to get an image stable for a longer time by application of an electrical field kept by a capacitor under powerless conditions, respectively.

The invention claimed is:
1. A dispersion which is useful for electrophoretic displays comprising
   α) a bis-oxodihydro-indolylene-benzodifuranone colourant of the formula I

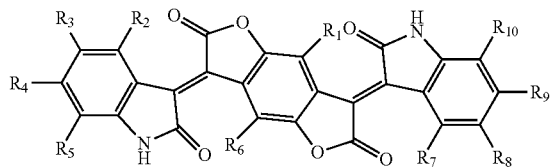

(I)

wherein $R_1$ and $R_6$ are each independently of the other H, $CH_3$, $CF_3$, F or Cl;

$R_2$, $R_3$, $R_4$, $R_5$, $R_7$, $R_8$, $R_9$ and $R_{10}$ are each independently of all others H, halogen, $R_{11}$, COOH, COOR$_{11}$, COO$^-$, CONH$_2$, CONHR$_{11}$, CONR$_{11}$R$_{12}$, CN, OH, OR$_{11}$, OOCR$_{11}$, OOCNH$_2$, OOCNHR$_{11}$, OOCNR$_{11}$R$_{12}$, NO$_2$, NH$_2$, NHR$_{11}$, NR$_{11}$R$_{12}$, NHCOR$_{12}$, NR$_{11}$COR$_{12}$N=CH$_2$, N=CHR$_{11}$, N=CR$_{11}$R$_{12}$, SH, SR$_{11}$, SOR$_{11}$, SO$_2$R$_{11}$, SO$_3$R$_{11}$, SO$_3$H, SO$_3^-$, SO$_2$NH$_2$, SO$_2$NHR$_{11}$ or SO$_2$NR$_{11}$R$_{12}$; and $R_2$ and $R_3$, $R_3$ and $R_4$, $R_4$ and $R_5$, $R_7$ and $R_8$, $R_8$ and $R_9$, and/or $R_9$ and $R_{10}$ can also be linked together by a direct bond or an O, S, NH or NR$_{11}$ bridge;

$R_{11}$ and $R_{12}$ are each independently of the other $C_1$-$C_{12}$ alkyl, $C_1$-$C_{12}$ cycloalkyl, $C_1$-$C_{12}$ alkenyl, $C_1$-$C_{12}$ cycloalkenyl or $C_1$-$C_{12}$ alkinyl, each of which is uninterrupted or interrupted by oxygen, NH, NR$_{13}$ and/or sulfur in two or more fragments each comprising at least 2 C atoms, and each of which is also unsubstituted or substituted one or more times with COOH, COOR$_{13}$, COO$^-$, CONH$_2$, CONHR$_{13}$, CONR$_{13}$R$_{14}$, CN, oxo, OH, OR$_{13}$, OOCR$_{13}$, OOCNH$_2$, OOCNHR$_{13}$, OOCNR$_{13}$R$_{14}$, NR$_{13}$, NH$_2$, NHR$_{13}$, , NR$_{13}$R$_{14}$, NHCOR$_{14}$, NR$_{13}$COR$_{14}$, N=CH$_2$, N=CHR$_{13}$, N=CR$_{13}$R$_{14}$, SH, SR$_{13}$, SOR$_{13}$, SO$_2$R$_{13}$, SO$_3$R$_{13}$, SO$_3$H, SO$_3^-$, SO$_2$NH$_2$, SO$_2$NHR$_{13}$, SO$_2$NR$_{13}$R$_{14}$or halogen; or $C_7$-$C_{12}$ aralkyl, $C_1$-$C_{11}$ heteroaryl or $C_6$-$C_{12}$ aryl, each of which is unsubstituted or substituted one or more times with COOH, COOR$_{13}$, COO$^-$, CONH$_2$, CONHR$_{13}$, CONR$_{13}$R$_{14}$, CN, OH, OR$_{13}$, OOCR$_{13}$, OOCNH$_2$, OOCNHR$_{13}$, OOCNR$_{13}$R$_{14}$, NO$_2$, NH$_2$, NHR$_{13}$, NR$_{13}$R$_{14}$, NHCOR$_{14}$, NR$_{13}$COR$_{14}$, N=CH$_2$, N=CHR$_{13}$, N=CR$_{13}$R$_{14}$, SH, SR$_{13}$, SOR$_{13}$, SO$_2$R$_{13}$, SO$_3$R$_{13}$, SO$_3$H, SO$_3^-$, SO$_2$NH$_2$, SO$_2$NHR$_{13}$, SO$_2$NR$_{13}$R$_{14}$ or halogen; and each $R_{13}$ or $R_{14}$ is, independently of any other $R_{13}$ or $R_{14}$, $C_1$-$C_6$ alkyl, benzyl or phenyl, each of which is unsubstituted or substituted one or more times with substituents as defined above, with the proviso that the total number of atoms in any substituent of $R_{13}$ and $R_{14}$ is from 1 to 8; whereby pairs of substituents selected from the group consisting of all $R_{13}$ and $R_{14}$ can optionally be linked together by a direct bond or an O, S, NH or NR$_{11}$ bridge so as to form rings, or a cis-trans isomer thereof or a salt of such colourant or isomer having a salt-forming group, β) a polymeric dispersant comprising modified poly(meth) acrylate polymers obtained by the process comprising the steps a1) polymerizing in a first step one or more ethylenically unsaturated monomers in the presence of at least one nitroxylether having the structural element of the formula

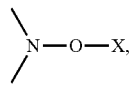

wherein X represents a group having at least one carbon atom and is such that the free radical X● derived from X is capable of initiating polymerization; or a2) polymerizing in a first step one or more ethylenically unsaturated monomers in the presence of at least one stable free nitroxyl radical of the formula

and a free radical initiator; wherein at least one monomer used in the steps a1) or a2) is a $C_1$-$C_6$ alkyl or hydroxy $C_1$-$C_6$ alkyl ester of acrylic or methacrylic acid; and a second step b) comprising the modification of the polymer or copolymer prepared under a1) or a2) by a transesterification reaction, an amidation, hydrolysis or anhydride modification or a combination thereof, and γ) a solvent which is suitable for dispersions used in electrophoretic displays.

2. A dispersion according to claim 1 wherein the colourant is a pigment of the formula 1

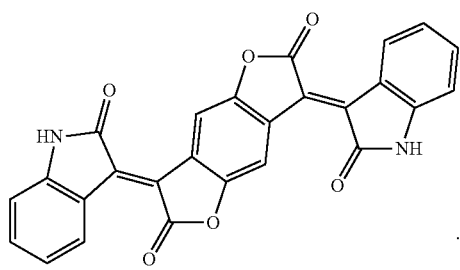

3. A dispersion according to claim 1 wherein the colourant is a sulfonic acid of the formula 2a

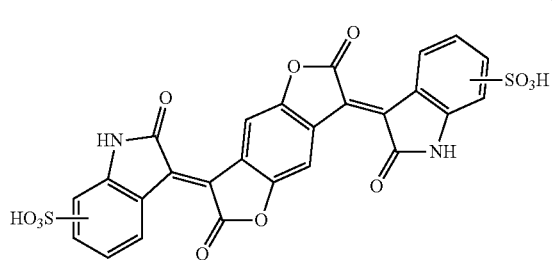

or a salt thereof and/or a cis/trans-isomer of said acid or salt.

4. A dispersion according to claim 1 wherein the polymeric dispersant is selected from modified poly(meth)acrylate polymers of the formula II

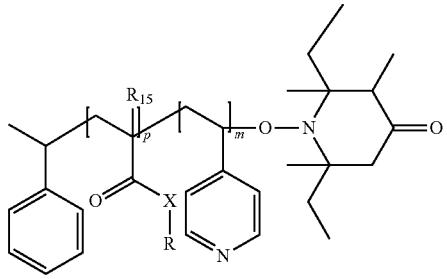

wherein X represents oxygen or the group NH, m is 0 or 10-20, p is 60-90, $R_{15}$ is hydrogen or methyl, and R represents alkyl having up to 30 carbon atoms wherein one or more carbon atoms may be replaced by oxygen and which is unsubstituted or substituted by dimethylamino or trimethylamino with the proviso that the group X—R is not the same in all (p) moieties of the partial formula —$CH_2$—$C(R_{15})$(CO—X—R)— present in formula I, and salts of such polymers having a salt-forming group.

5. A dispersion according to claim 1 wherein the solvent is dodecane.

6. A dispersion according to claim 1 wherein the dispersed particles have a diameter of 200-800 nm.

7. A bis-oxodihydro-indolylene-benzodifuranone colourant of the formula 2a depicted in claim 3 or a salt thereof and/or a cis/trans-isomer of said acid or salt.

8. A dispersion according to claim 1 wherein the polymeric dispersant is selected from modified poly(meth)acrylate polymers of the formula II

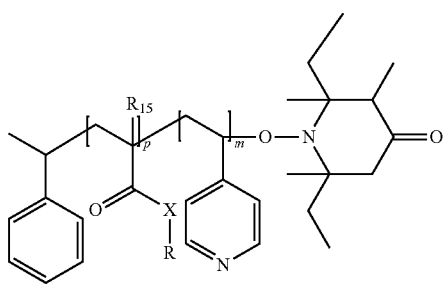

wherein X represents oxygen or the group NH, m is 0 or 10-20, p is 60-90, $R_{15}$ is hydrogen or methyl, and R represents alkyl having up to 20 carbon atoms wherein one or more carbon atoms may be replaced by oxygen and which is unsubstituted or substituted by dimethylamino or trimethylamino with the proviso that the group X—R is not the same in all (p) moieties of the partial formula —$CH_2$—$C(R_{15})$(CO—X—R)— present in formula I in claim 1 and the different groups X—R are randomly distributed along the polymer chain, or a salt of such dispersant having a salt-forming group.

9. A dispersant according to claim 8 wherein in up to 20% of said p moieties of the partial formula —$CH_2$—$C(R_{15})$(CO—X—R)— R is unsubstituted $C_1$-$C_6$ alkyl, while in the remaining moieties R is different from unsubstituted $C_1$-$C_6$ alkyl.

10. An electrophoretic display comprising a dispersion of a bis-oxodihydro-indolylene-benzodifuranone colourant of the formula I and a polymeric dispersant as defined in claim 1 and a solvent which is suitable for dispersions used in electrophoretic displays.

* * * * *